US010293338B2

(12) United States Patent
Foucault

(10) Patent No.: US 10,293,338 B2
(45) Date of Patent: May 21, 2019

(54) METHOD AND DEVICE FOR TRANSFERRING PART OF A LIQUID HOUSED IN A CONTAINER

(71) Applicant: BIOMERIEUX, Marcy L'etoile (FR)

(72) Inventor: Frederic Foucault, Marcy L'etoile (FR)

(73) Assignee: BIOMERIEUX, Marcy L'etoile (FR)

( * ) Notice: Subject to any disclaimer, the term of this patent is extended or adjusted under 35 U.S.C. 154(b) by 134 days.

(21) Appl. No.: 15/032,423

(22) PCT Filed: Nov. 13, 2014

(86) PCT No.: PCT/FR2014/052891
§ 371 (c)(1),
(2) Date: Apr. 27, 2016

(87) PCT Pub. No.: WO2015/071599
PCT Pub. Date: May 21, 2015

(65) Prior Publication Data
US 2016/0250630 A1    Sep. 1, 2016

(30) Foreign Application Priority Data

Nov. 14, 2013 (FR) ..................................... 13 61112

(51) Int. Cl.
| | |
|---|---|
| *G01N 33/49* | (2006.01) |
| *B01L 99/00* | (2010.01) |
| *B01L 3/00* | (2006.01) |
| *G01N 1/34* | (2006.01) |

(52) U.S. Cl.
CPC .............. *B01L 3/502* (2013.01); *G01N 1/34* (2013.01); *G01N 33/491* (2013.01); *B01L 3/50825* (2013.01); *B01L 2200/0631* (2013.01); *B01L 2300/042* (2013.01); *B01L 2300/044* (2013.01); *B01L 2300/0672* (2013.01); *B01L 2300/0681* (2013.01); *B01L 2300/0832* (2013.01); *B01L 2300/0861* (2013.01); *B01L 2400/0478* (2013.01); *B01L 2400/0487* (2013.01); *B01L 2400/0683* (2013.01)

(58) Field of Classification Search
None
See application file for complete search history.

(56) References Cited

U.S. PATENT DOCUMENTS

| 5,603,695 A | 2/1997 | Erickson |
|---|---|---|
| 2002/0177819 A1* | 11/2002 | Barker ................ A61M 5/3234 604/232 |
| 2004/0014203 A1 | 1/2004 | Wickstead et al. |
| 2009/0082751 A1 | 3/2009 | Reynolds et al. |
| 2009/0131864 A1 | 5/2009 | Pickhard |

OTHER PUBLICATIONS

International Search Report dated Mar. 4, 2015, corresponding to International Patent Application No. PCT/FR2014/052891.

* cited by examiner

*Primary Examiner* — Paul S Hyun
(74) *Attorney, Agent, or Firm* — Ladas & Parry LLP; Malcolm J. MacDonald

(57) ABSTRACT

A device for transferring a portion of a liquid contained in a container, the device having a hollow needle for penetrating through the plug of the container; a pressure chamber for pressurizing a fluid, the chamber having the needle passing therethrough and being provided with a septum; and an approach system for causing the hollow needle and the septum to approach each other so as to increase the pressure of the fluid as a result of the approach.

20 Claims, 5 Drawing Sheets

METHOD AND DEVICE FOR TRANSFERRING PART OF A LIQUID HOUSED IN A CONTAINER

This application is a 371 of PCT/FR2014/052891, filed on Nov. 13, 2014, which claims priority to French Patent Application No. 1361112, filed Nov. 14, 2013.

The present invention relates to the technical field of transferring a portion of a liquid in the general sense, contained in a container in the general sense, and in particular provided with a plug that can be penetrated by a hollow needle.

The invention finds an application that is particularly but not exclusively advantageous in the field of biology, and in particular in extracting plasma from blood contained in a container provided with a plug.

In the preferred field of application of the invention, it is common practice to recover a blood sample in a container that is in the form of a tube closed by a plug, such as a septum, that can be penetrated by a hollow needle. Numerous solutions have been proposed for obtaining plasma from such a blood sample. Among other techniques, those solutions rely on two specific techniques for extracting plasma from whole blood, namely filtering and centrifuging.

Isolating blood plasma by centrifuging requires the use of equipment that is complex and expensive firstly for the purpose of separating the components of blood as a function of their density differences by subjecting them to centrifugal force, and secondly for extracting the plasma from the portion of the blood containing the red blood cells after they have had time to settle. Independently of the need to have recourse to a centrifuge and to centrifuge tubes, that technique requires centrifuging time that is relatively long, and it presents difficulty in defining the centrifugal force needed for obtaining plasma that does not contain any formed elements of blood.

Extracting plasma by filtering requires the use of a blood separation medium. The article "Micro-scale blood plasma separation: from acoustophoresis to egg-beaters", published in "The Royal Society of Chemistry 2013", summarizes the various known solutions for achieving plasma separation at microscopic scale. An analysis of known prior techniques shows that there is no simple solution, without risk of contamination, for extracting a non-negligible quantity of liquid relatively quickly from a closed container containing a sample of liquid such as blood, for the purpose of subjecting the extracted liquid to separation.

U.S. Pat. No. 5,603,695 describes a device that enables a buffer solution contained in a cartridge to be added to an anesthetic contained in a carpule including a septum that can be penetrated by a needle and a piston that can be moved by a syringe.

The cartridge is provided with a needle supported by a membrane and provided with an abutment. Relative movement between the carpule and the cartridge causes the septum to be perforated by the needle that is moved so as to pass through the membrane and come into contact, via its abutment, against the membrane. The needle thus ensures that the buffer solution is transferred into the carpule. The cartridge is mounted on the carpule and is fitted with a wall provided with a through needle that communicates both with the buffer solution and also with a chamber defined between the wall and the septum of the carpule. During the relative movement of the carpule, the needle perforates the septum of the carpule enabling the buffer solution to be transferred into the carpule. Although the device described by that patent enables a buffer solution contained in a cartridge to be added to a medium contained in a carpule, such a device does not enable a portion of a liquid contained in a container to be extracted easily and quickly.

An object of the invention is thus to remedy the drawbacks of the prior art by proposing a novel technique for extracting a portion of a liquid contained in a container in a manner that is simple and without risk of contamination, and in a time that is relatively short.

Another object of the invention is to propose a method that makes it possible to extract several non-negligible quantities of liquid contained in a single container.

In order to achieve such objects, the invention provides a method of transferring a portion of a liquid contained in a container provided with a plug. According to the invention, the method consists in:

using a hollow needle passing through the plug of the container to put the inside of the container into communication with a sealingly chamber for pressurizing a fluid, which chamber is provided with a septum that is penetrable by needle and presents a volume that is variable as a result of relative movement between the hollow needle and the septum that is penetrable by needle;

causing the hollow needle and the septum that is penetrable by needle to approach each other over a determined stroke so as to increase the pressure inside the chamber and consequently inside the container by transferring the fluid via the hollow needle and reaching a transfer pressure immediately prior to the hollow needle passing through the septum; and continuing to cause the hollow needle and the septum that is penetrable by needle to approach each other so that the hollow needle passes through the septum so as to open out into a liquid distribution chamber at a pressure that is lower than the transfer pressure so that under the effect of this pressure difference a portion of the liquid is transferred through the hollow needle from the container into said distribution chamber.

In addition and in combination, the method of the invention may include at least one of the following additional characteristics:

ensuring that the liquid transferred into the distribution chamber flows through a filter system in order to extract a portion of the liquid;

for a container containing blood, ensuring that the portion of the liquid that is extracted is plasma;

after plasma has been extracted, recovering the filter system for analysis purposes;

the fluid in the pressure chamber comprises a medium for processing the liquid contained in the container;

in order to ensure that plasma is extracted, reaching a transfer pressure that lies in the range atmospheric pressure to atmospheric pressure plus 3 bars;

at the end of the fluid flowing into the distribution chamber, enabling the hollow needle and the septum that is penetrable by needle to be separated relative to each other in such a manner that the hollow needle communicates with the inside of the pressure chamber so as to enable the fluid under pressure in said chamber to cause the liquid contained in the needle to be returned into the container;

adapting the pressure in the pressure chamber as a function of the volume of fluid contained inside the container;

adjusting the pressure in the pressure chamber by ensuring that the pressure chamber is set to atmospheric pressure so long as the spacing between the hollow needle and the septum that is penetrable by needle does not reach a determined value;

putting the inside of the container into communication with the pressure chamber, by guiding the container so that the hollow needle carried by the pressure chamber and opening out therein, passes through the plug of the container; and during a calibration stage prior to putting the container into communication with the pressure chamber, in placing the septum and the hollow needle in a position of proximity and in injecting a pressurizing fluid into the chamber through the hollow needle.

Another object of the invention is to propose a simple device for extracting a portion of a liquid contained in a container in a manner that is without risk of contamination, and in a time that is very short.

In order to achieve such an object, the device of the invention for transferring a portion of a liquid contained in a container provided with a plug comprises:

a hollow needle provided with a proximal end with a distal end for penetrating through the plug of the container;

a pressure chamber for pressurizing a fluid and having the proximal end of the hollow transfer needle passing therethrough, the chamber being provided with a septum positioned to be penetrable by the proximal end of the needle after the needle has moved, the chamber being sealingly and separated by the septum from a liquid distribution chamber into which the proximal end of the hollow needle can open out; and an approach system for causing the hollow needle and the septum to approach each other so as to increase the pressure of the fluid as a result of said approach, the approach system being controlled to move over a determined stroke so that in a first stage the pressure inside the sealingly chamber is increased up to a transfer pressure immediately prior to the hollow needle passing through the septum, and in a second stage the hollow needle passes through the septum to open out into the liquid distribution chamber that is at a pressure lower than the transfer pressure so that under the effect of this pressure difference a portion of the liquid is transferred from the container into said distribution chamber.

Various other characteristics appear from the following description made with reference to the accompanying drawings which, by way of non-limiting example, show embodiments of the invention.

Figure 1:
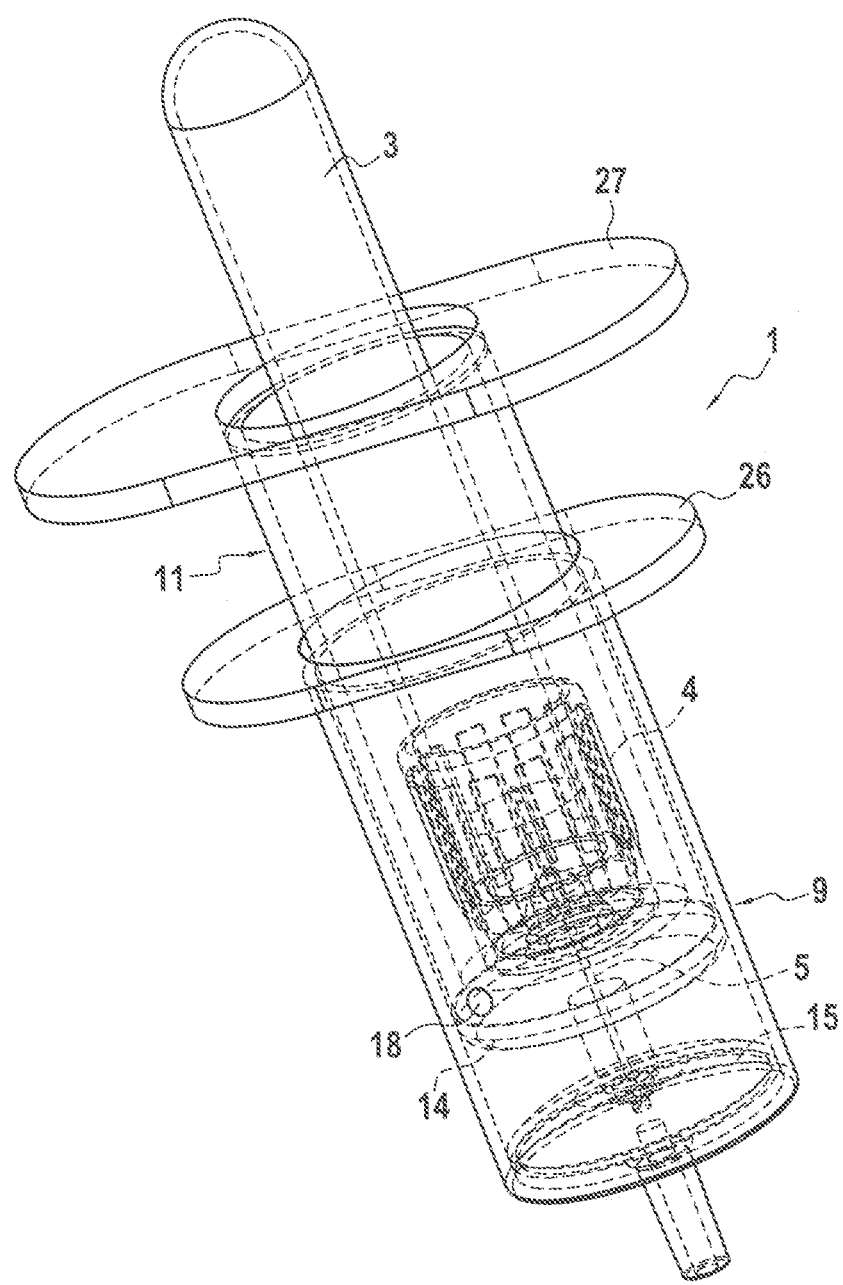
FIG. 1 is a perspective view showing an embodiment of the device in accordance with the invention for extracting a liquid contained in a container.
Figure 2:
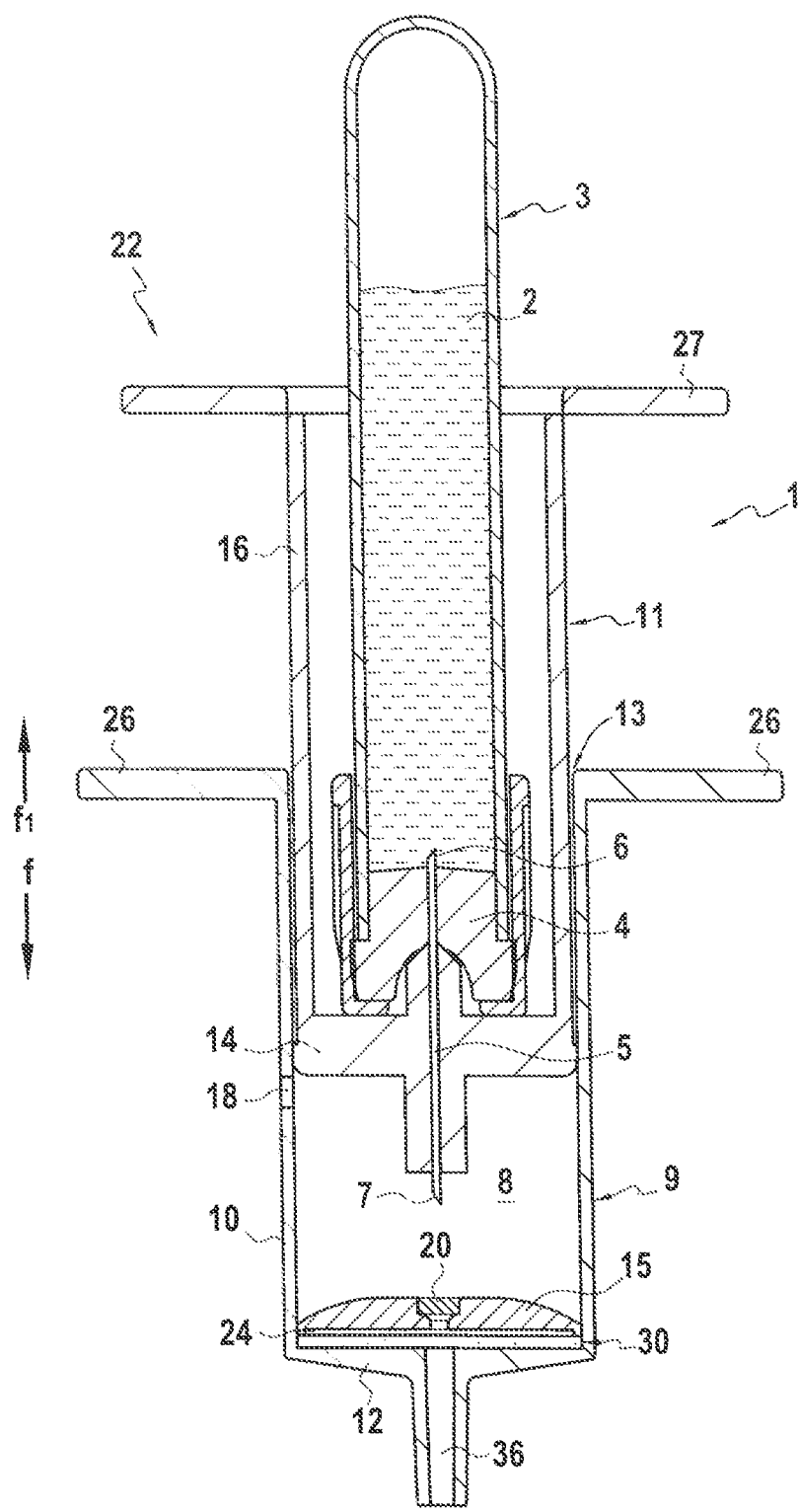
FIG. 2 is an elevation view in section showing the device in accordance with the invention in an initial extraction position.

As can be seen more clearly in FIGS. 1 and 2, the invention relates to a device 1 for transferring a portion of a liquid 2 contained in a container 3 that is conventionally in the form of a tube that is hermetically closed by a plug 4. In a preferred application, the container 3 is a tube for taking a blood sample under vacuum, but it is clear that the device of the invention is suitable for extracting a portion of the contents of a container that is in a form other than a sample tube.

Figure 5:
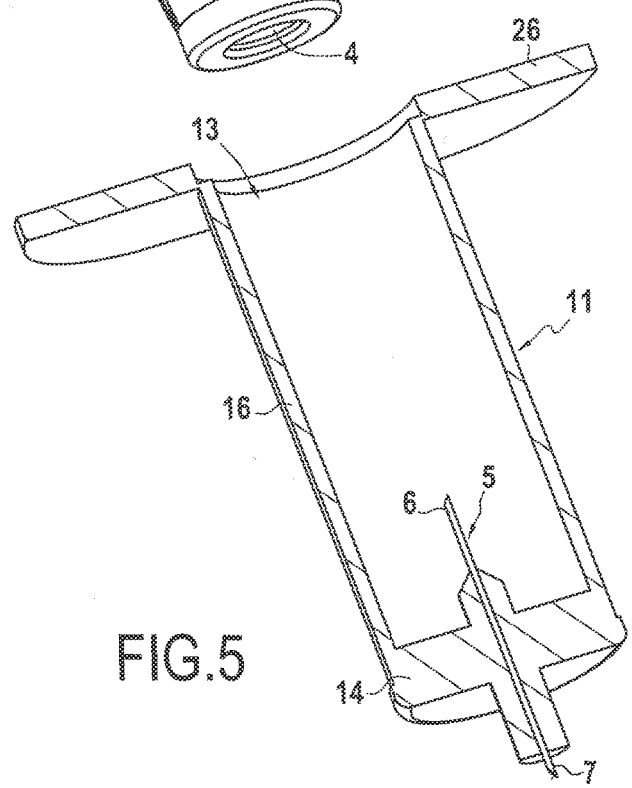
FIG. 5 is a perspective view showing how a container is mounted on the piston of the extraction device in accordance with the invention.

According to a characteristic of the invention, the container 3 is suitable for having a hollow needle 5 penetrating therein with a portion of the liquid contained inside the container being transferred or extracted through the needle. In the preferred application to a blood sample tube, the plug 4, such as a septum, can be penetrated by the hollow needle 5. As can be seen more clearly in FIGS. 2 and 5, the hollow needle 5 has a distal end 6 for penetrating through the plug 4 of the container and a proximal end 7 that performs a function that is described in greater detail in the description below. In the example shown in FIG. 5, the plug 4 of the container 3 has the distal end 6 of the hollow needle 5 passed therethrough as a result of relative movements of the container 3 and the hollow needle 5 towards each other. Naturally, provision could be made for the plug 4 to be fitted ab initio with the hollow needle 5.

In accordance with the invention, the device 1 includes a sealingly pressure chamber 8 for pressurizing a fluid contained in such a chamber. This pressure chamber 8 is defined between a cylinder 9 and a piston 11 that co-operates in sealingly manner with the cylinder 9. As can be seen in FIGS. 1 and 2, the cylinder 9 is in the form of a tube 10 of circular right cross-section that is provided with an end wall 12 at one end and with an opening 13 at its opposite end for passing the piston 11. The piston 11 has a rigid partition 14 optionally provided with a gasket and presenting a shape that is complementary to the tube 10 of the cylinder so that they co-operate together in sealingly manner. The tube 10 is provided at its end wall 12 with a closure partition 15 serving to co-operate with the rigid partition 14 of the piston and with the wall of the tube 10 situated between these partitions so as to define the sealingly pressure chamber 8 of variable volume.

According to a preferred embodiment characteristic, the piston 11 is provided with the hollow needle 5 having its distal end 6 facing away from the pressure chamber 8 and projecting from one side of the rigid partition 14. According to an advantageous embodiment characteristic, the length of the distal end 6 of the hollow needle 5 that projects from the rigid partition 14 is sufficient to pass through the plug 4 and penetrate into the inside of the container 3. The proximal end 7 of the hollow needle 5 extends towards the pressure chamber 8 and projects from the other side of the rigid partition 14. The hollow needle 5 is thus fastened in sealingly manner by any appropriate means to the rigid partition 14 and it passes right through it, projecting from the partition on both sides thereof.

According to another preferred embodiment characteristic, the piston 11 has a protective sleeve 16 surrounding the distal end 6 of the hollow needle 5 at a distance so as to define internally a reception volume for at least a portion of the container 3. Advantageously, the protective sleeve 16 extends from the rigid partition 14 over a height that is greater than the length of the distal end 6 of the hollow needle 5 so as to avoid any injury by this portion of the hollow needle.

From the above description, it can be seen that the piston 11 and the cylinder 9 are mounted to move relative to each other in translation in an approach direction represented by arrow f and in an opposite, separation direction represented by arrow f1. Thus, moving the piston 11 in the approach direction leads to a reduction in the volume of the chamber 8 and consequently to an increase in the pressure of the fluid inside the chamber 8.

It should be observed that while the device 1 is in use with the plug 4 of the container 3 having the distal end 6 of the hollow needle 5 passing therethrough, this pressure chamber 8 communicates via the hollow needle 5 with the inside of the container 3 so that its pressure has a value that is identical to the pressure in the chamber 8. Thus, an increase in the pressure of the fluid inside the chamber 8 leads to a corresponding increase of the pressure of the fluid inside the container 3.

According to an advantageous embodiment characteristic, the device 1 of the invention includes a system 18 for adjusting the pressure in the pressure chamber 8 and consequently in the container 3. In the example shown, the system 18 for adjusting the pressure in the pressure chamber 8 is provided by means of a through hole formed in the tube 10 to put the chamber 8 to atmospheric pressure so long as the piston 11 occupies a position set back from the hole 18. Thus, as soon as the position of the piston 11 is such that the chamber no longer communicates with the hole 18, the fluid can be compressed. This system 18 serves to adjust the pressure in the pressure chamber 8 by ensuring that it is set to atmospheric pressure so long as the spacing between the hollow needle 5 and a septum 20 does not reach a value as determined by the position of the hole 18.

Advantageously, the system 18 enables the value of the pressure in the pressure chamber 8 to be adjusted to a value that is variable. In an embodiment, the system 18 includes a slide mounted to move in the travel direction of the piston and provided with a hole that is adapted to communicate with a slot formed in the tube 10 and that is closed by the slide with the exception of the hole. Moving the slide in translation adjusts the position of the hole for communicating with atmospheric pressure and consequently adjusts the volume of the chamber 8. In another embodiment, the closure partition 15 of the cylinder 9 is mounted to be movable relative to the tube 10 (e.g. by screw fastening) so as to enable the volume of the chamber 8 to be varied.

According to a characteristic of the invention, the pressure chamber 8 is provided with a septum 20 that is positioned so as to be penetrable by the proximal end 7 of the hollow needle 5 after it has been moved in the approach direction. For this purpose, the closure partition 15 of the cylinder 9 is provided with a septum 20 that is thus positioned facing the proximal end 7 of the hollow needle 5. For example, the septum 20 may be made in various ways, including by bi-injection, by overmolding, or by being inserted mechanically after molding.

Advantageously, the device 1 of the invention includes a system for guiding movement in translation of the proximal end 7 of the hollow needle 5 upstream from the septum 20. This guide system, which is not shown, is adapted to position the hollow needle so that the proximal end 7 passes correctly through the septum 20.

The device 1 of the invention includes a system 22 for causing the hollow needle 5 and the septum 20 to approach each other in such a manner that over a first stroke the pressure of the fluid inside the chamber 8 is increased up to a transfer pressure, and then over a subsequent stroke following the first, the hollow needle 5 passes through the septum 20 so that the hollow needle 5 leads into a liquid distribution chamber 24 that is at a pressure that is lower than the transfer pressure. The distribution chamber 24 is thus separated from the pressure chamber 8, in particular by means of the septum 20, which is in contact on one side with the distribution chamber 24 and on its opposite side with the pressure chamber 8.

The system 22 for causing the hollow needle 5 and the septum 20 to approach each other exerts a mechanical thrust force on the hollow needle in the direction f and/or on the septum 20 in the direction f1. In the variant embodiment that is shown in the drawings, the approach system 22 is of manual type, however it is clear that the movement between the hollow needle 5 and the septum 20 could be motor-driven.

In order to facilitate manual application of a thrust force, the tube 10 of the cylinder 9 includes two external grip lugs 26 level with its opening 13, while the protective endpiece 16 is provided remote from the rigid partition 14 with a thrust collar 27. Conventionally, a thrust force is exerted on the collar 27 of the sleeve of the piston 11, while the cylinder 9 is held in position by the lugs 26. In this embodiment, a system is provided for viewing the penetration of the piston 11 into the cylinder 9 in order to control the amount of manual pressure that is applied. For example, graduations are marked on the piston 11 in order to visualize the penetration of the piston 11.

Figure 3:
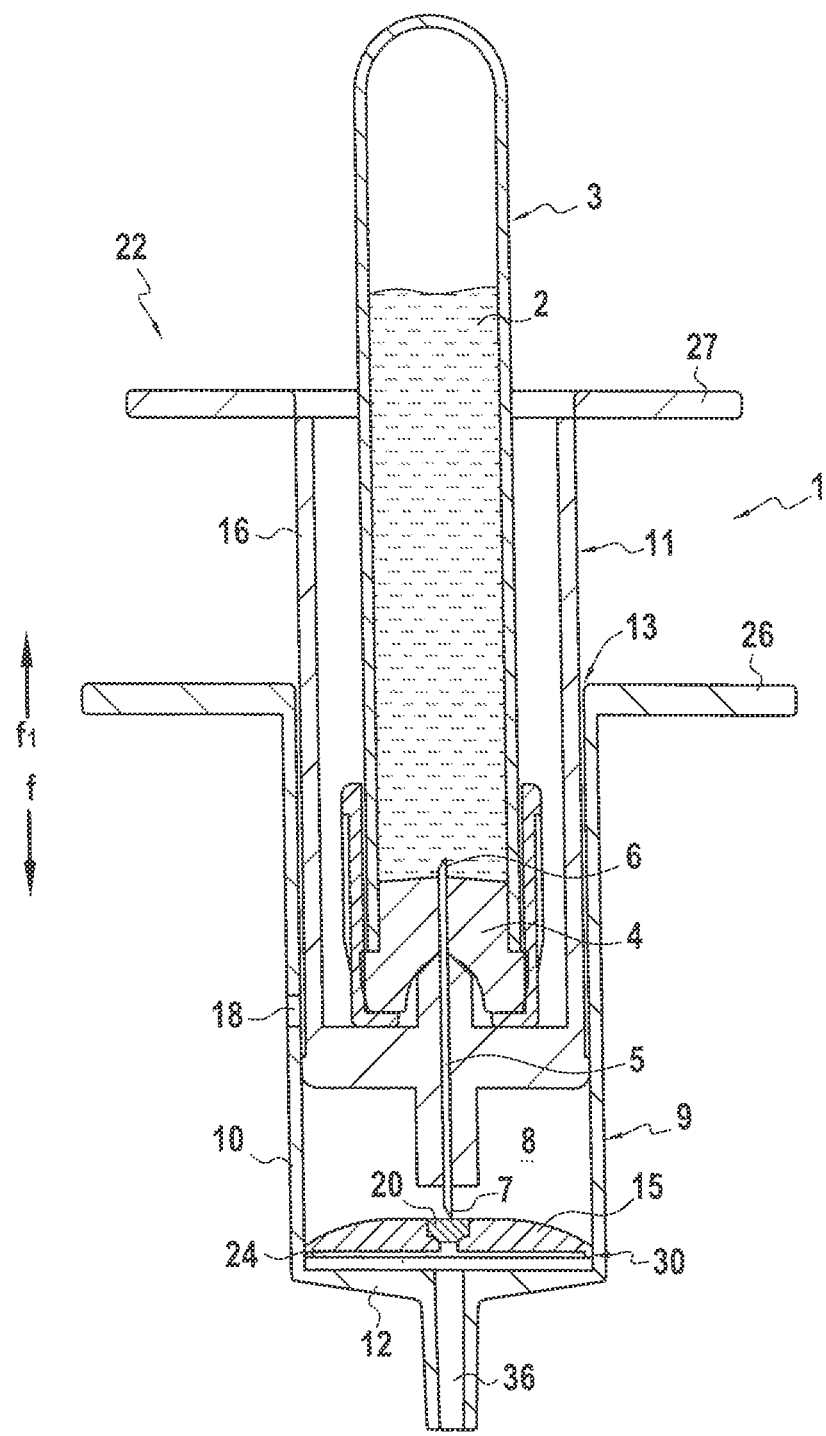
FIG. 3 is an elevation view in section showing the device in accordance with the invention in an intermediate extraction position.
Figure 4:
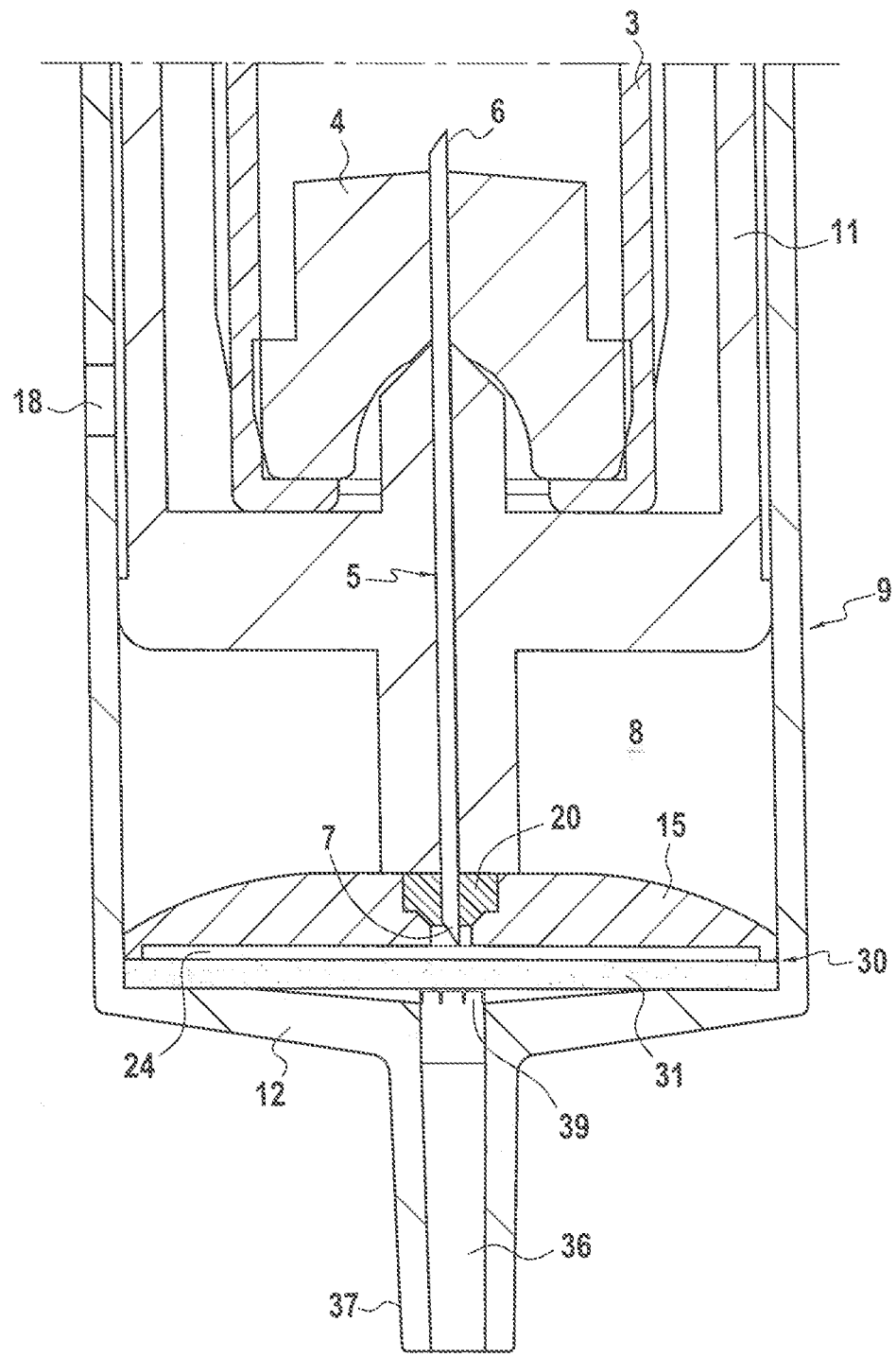
FIG. 4 is an elevation view on a larger scale in section showing the device in accordance with the invention in a position for extracting a portion of the liquid contained in a container.

From the above description, it can be seen that the piston 11 is suitable for occupying:

a first position as shown in FIG. 2 in which the chamber 8, and consequently the container 3, are set to atmospheric pressure via the hole 18;

a second position, as shown in FIG. 1, enabling the pressure inside the chamber 8, and consequently inside the container 3, to be increased as the partitions 14 and 15 approach each other;

a third position as shown in FIG. 3, in which the hollow needle 5 is positioned immediately prior to passing through the septum 20; and a fourth position as shown in FIG. 4 in which the hollow needle 5 passes through the septum 20 and communicates with the distribution chamber 24, which is advantageously at atmospheric pressure.

According to an advantageous embodiment characteristic, the device 1 of the invention includes a stop for limiting the approach movement of the partitions 14 and 15 in a predetermined position in which the proximal end 7 of the hollow needle 5 passes through the septum 20 so as to open out into the distribution chamber 24 (FIG. 4). In the example shown in FIG. 4, the bottom end of the partition 14 comes directly into abutment against the partition 15. Another abutment system (not shown) could be made in any other suitable manner, e.g. by an arrangement on the sleeve 16 for coming to bear against the lugs of the cylinder 10.

According to an advantageous embodiment characteristic that can be better understood from the description below, the approach system 22 also serves to separate the hollow needle 5 relative to the septum 20 that can be penetrated by the needle. This system 22, which is adapted to separate the hollow needle 5 from the septum 20, exerts a mechanical thrust force on the hollow needle 5 in the direction f1 and/or on the septum 20 in the direction f. In the embodiment variant shown in the drawings, the separation system 22 is of the manual type, but it is clear that the movement between the hollow needle 5 and the septum 20 could be motor-driven.

In an advantageous variant embodiment, the distribution chamber 24 is provided with a filter system 30 for ensuring that a liquid phase is extracted from the liquid transferred into said chamber. In a preferred application of the invention, the filter system 30 is adapted to extract plasma as a portion of liquid extracted from the container 3 containing blood.

As can be seen more clearly in FIG. 4, the filter system 30 comprises a filter medium 31 held in position by a support structure such as the end wall 12 of the cylinder 9. Advantageously, the filter medium 31 is mounted inside the distribution chamber 24 so as to extend at a distance from the septum, and in particular from the closure partition 15. Thus, the distribution chamber 24 presents a volume between the closure partition 15 and the top surface of the filter medium 31 for recovering the liquid leaving the proximal end 7 of the hollow needle 5. This distribution chamber 24 serves to distribute the liquid over the entire surface of the filter medium 31.

Figure 6:
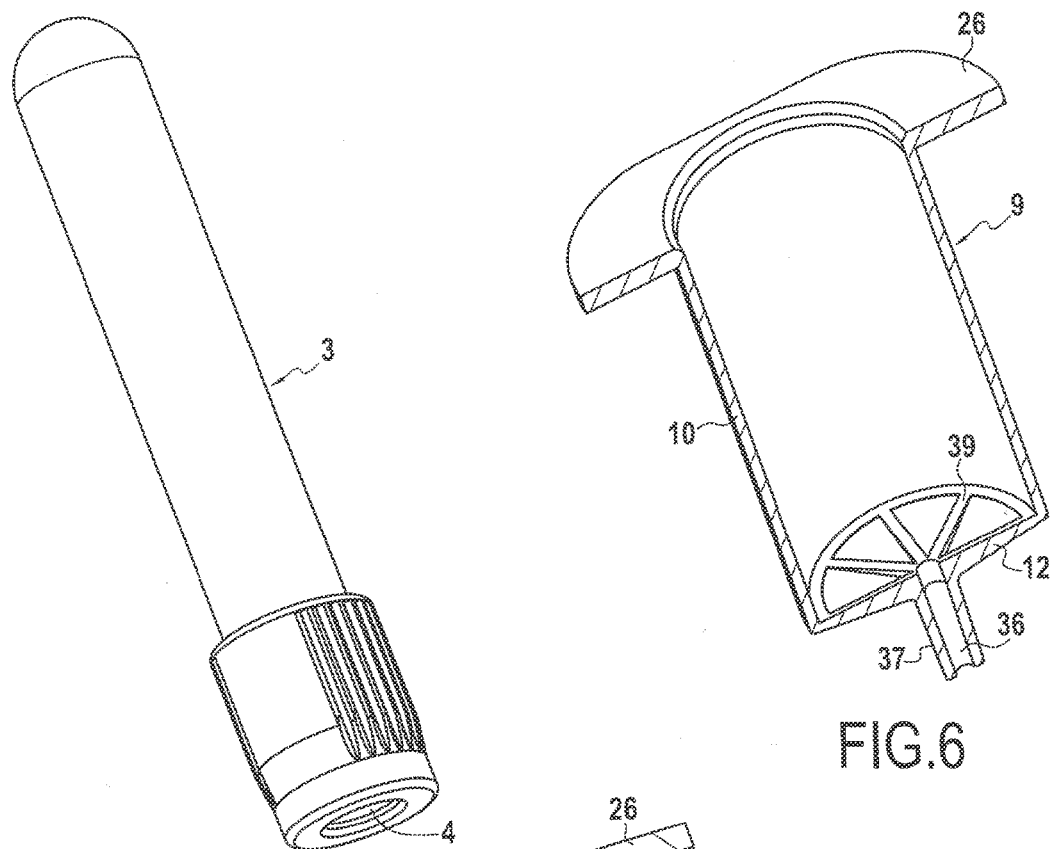
FIG. 6 is a section view of the cylinder for receiving the piston of the extraction device in accordance with the invention.

Advantageously, the end wall 12 of the cylinder 9 on which the filter medium 31 rests is curved towards an outlet orifice 36 for the filtered liquid, which orifice is formed in a tip 37 projecting from the end wall 12. The end wall 12 on which the filter medium 31 rests is preferably provided with ribs or spokes 39 on the end wall 12 so as to avoid the filter medium 31 clogging and so as to limit head loss (FIG. 6).

In the example shown in the drawings, the distribution chamber 24 is defined by a portion of the piston-receiving cylinder 9. It should be observed that it is possible to envisage making the chamber 24 as a separate unit that contains the filter system and that is fitted to the cylinder 9. A releasable connection for the distribution chamber 24 may be provided, in particular in order to make it easy to recover the filter medium, should it need to be subjected to subsequent analyses. Usually, the complete device is in the form of a disposable consumable, without there being any manipulation of the filter medium 31, such that such a releasable connection need not be provided.

The way in which the device 1 in accordance with the invention is used for transferring a portion of a liquid contained in a container 3 stems directly from the above description.

The transfer method consists in using the hollow needle 5 to put the inside of the container 3 into communication with the pressure chamber 8. For this purpose, the container 3 is inserted into the sleeve 16 until the distal end 6 of the hollow needle 5 passes through the plug 4. If the pressure chamber 8 is at atmospheric pressure because of the hole 18, then the container 3 is also placed at atmospheric pressure (FIG. 2).

Thereafter, the method consists in causing the hollow needle 5 to approach the septum 20 in order to increase the pressure inside the chamber 8, and consequently inside the container 3. Applying a thrust force to the piston 11 leads to it moving in the direction f, to a position beyond the hole 18, in which position the chamber 8 and the container 3 together form a hermetically sealed enclosure. Continued movement of the piston 11 in the direction f enables the pressure of the fluid to be increased with some of the fluid being transferred into the container 3 via the hollow needle 5. The piston 11 is moved along a stroke that is determined in such a manner that the piston 11 becomes located immediately in front of the passage for the hollow needle 5 through the septum 20. In this position, as shown in FIG. 3, the pressure inside the chamber 8 and the container 3 reaches a desired pressure value referred to as the "transfer" pressure. Typically, when the liquid contained in the container 3 is blood from which an extraction of plasma is desired, the transfer pressure lies in the range atmospheric pressure (in particular standard atmospheric pressure at sea level, namely $1.013 \times 10^5$ pascals (Pa)) to atmospheric pressure plus 3 bars.

The method then consists in continuing to cause the hollow needle 5 to approach the septum 20 so that the proximal end 7 of the hollow needle 5 passes through the septum 20 and opens out into the distribution chamber 24 (FIG. 4). Insofar as the pressure in this distribution chamber 24 presents a pressure (typically atmospheric pressure) that is lower than the transfer pressure in the chamber 8 and the container 3, a portion of the liquid is transferred under the effect of this pressure difference from the container 3 into the distribution chamber 24. The liquid coming from the container 3 thus passes through the hollow needle 5 and flows from the proximal end 7 into the distribution chamber 24 until pressures are balanced between the container 3 and the distribution chamber 24.

When the distribution chamber 24 is provided with the filter system for extracting plasma from the blood recovered in the chamber 24, then the plasma flows out from the outlet orifice 36.

In an advantageous variant of this extraction method, the method consists, at the end of the fluid flowing into the distribution chamber 24, in moving the hollow needle 5 away from the septum 20 so as to extract the hollow needle 5 from the septum 20 and cause it to communicate via its proximal end 7 with the inside of the pressure chamber 8. Insofar as the fluid inside the chamber 8 presents a pressure that is higher than the pressure in the container 3, some of this fluid passes through the hollow needle 5, thereby causing the liquid contained in the needle 5 to return into the container 3. As a result, any liquid that might remain inside the needle is prevented from flowing out from the needle.

From the above description, it can be seen that the device 1 of the invention makes it possible in complete safety to extract a portion of a liquid contained in a container 3. This extraction is performed in a manner that is simple and inexpensive since it merely involves mechanical thrust. The device 1 is preferably for single use with each container. It should be observed that the filter system may be recovered for analysis purposes.

Advantageously, the device enables plasma to be extracted directly from a sample tube containing blood. Tests performed with a filter medium of section that is circular and of diameter of 20 mm have shown that the device 1 of the invention makes it possible to extract at least 200 microliters (µL) of plasma in less than 3 minutes. Furthermore, it has been possible to extract 200 µL of plasma three times in succession from a single 4 mL blood sample tube, changing the filter material each time.

It should be observed that by means of the system 22 the device 1 of the invention provides the advantage of being able to adapt the pressure in the pressure chamber 8 as a function of the volume of fluid contained inside the container 3, which volume of fluid may vary as a result of successive extractions or as a function of the levels to which containers 3 are filled. This regulation can be performed visually or in automatic manner.

In a particular embodiment, the fluid in the pressure chamber 8 is air. Naturally, the fluid in the chamber 8 could be of a different kind, such as a liquid that is not miscible with the liquid contained in the container 3. On the same lines, the fluid in the pressure chamber 8 may comprise a medium for processing the liquid contained in the container 3, while still containing a quantity of gas that is sufficient to enable compression/pressurization.

In a variant implementation of the device 1, a calibration stage may be performed in order to control the initial pressure in the pressure chamber 8. Prior to putting the container 3 into communication with the pressure chamber 8, this stage seeks to place the septum 20 and the hollow needle 5 in a position of proximity, i.e. the hollow needle is placed just before passing through the septum 20. A pressurizing fluid is injected into the chamber 8 through the hollow needle 5 and from its distal end 6, causing the movable piston 11 to be positioned at a determined distance from the closure partition 15 in order to define a chamber with a desired volume of fluid.

Although the device 1 of the invention is particularly adapted to extracting plasma from a blood sample, the device 1 of the invention makes it possible to extract a portion from any biological liquid contained in a container 3, such as urine, for example.

The invention is not limited to the embodiments that are described and shown, since various modifications can be applied thereto without going beyond the ambit of the invention.

The invention claimed is:

1. A method of transferring a portion of a liquid contained in a container provided with a plug, the method comprising:
    using a hollow needle passing through the plug of the container to put the inside of the container into communication with a pressure chamber for pressurizing a fluid, which pressure chamber is provided with a septum that is penetrable by the hollow needle and presents a volume that is variable as a result of relative movement between the hollow needle and the septum;
    causing the hollow needle and the septum to approach each other over a determined stroke so as to increase the pressure inside the pressure chamber, and, consequently, inside the container, until a transfer pressure is reached immediately prior to the hollow needle passing through the septum; continuing to cause the hollow needle and the septum to approach each other so that the hollow needle passes through the septum so as to open out into a distribution chamber at a pressure that is lower than the transfer pressure so that, under the effect of this pressure difference, a portion of the liquid is transferred through the hollow needle from the container into said distribution chamber;
    flowing the liquid transferred into the distribution chamber through a filter system in order to extract a portion of the liquid; and
    adapting the pressure in the pressure chamber as a function of the volume of fluid contained inside the container.

2. The method according to claim 1, wherein the container contains blood, and wherein a portion of the liquid that is extracted is plasma.

3. The method according to claim 2, comprising, after plasma has been extracted, recovering the filter system for analysis purposes.

4. The method according to claim 2, comprising, in order to ensure that plasma is extracted, reaching a transfer pressure that lies in a range of atmospheric pressure to atmospheric pressure plus 3 bars.

5. The method according to claim 1, wherein the fluid in the pressure chamber comprises a medium for processing the liquid contained in the container.

6. The method according to claim 1, comprising, at the end of the fluid flowing into the distribution chamber, separating the hollow needle and the septum from each other in such a manner that the hollow needle communicates with the inside of the pressure chamber so as to enable the fluid under pressure in said pressure chamber to cause any liquid contained in the hollow needle to be returned into the container.

7. The method according to claim 1, comprising adjusting the pressure in the pressure chamber to ensure that the pressure chamber is maintained at atmospheric pressure until the spacing between the hollow needle and the septum reaches a determined value.

8. The method according to claim 1, wherein the inside of the container is put into communication with the pressure chamber by guiding the container.

9. The method according to claim 1, further comprising a calibration stage wherein the septum and the hollow needle are placed in a position of proximity, and wherein a pressurizing fluid is injected into the pressure chamber through the hollow needle.

10. A device for transferring a portion of a liquid contained in a container provided with a plug, the device comprising:
    a hollow needle provided with a proximal end and with a distal end for penetrating through the plug of the container;
    a pressure chamber for pressurizing a fluid and having the proximal end of the hollow needle passing therethrough, the chamber being provided with a septum positioned to be penetrable by the proximal end of the hollow needle after the hollow needle has moved, the pressure chamber being sealed and separated by means of the septum from a distribution chamber into which the proximal end of the hollow needle can open out; and
    an approach system for causing the hollow needle and the septum to approach each other so as to increase the pressure of the fluid as a result of said approach, the approach system being controlled to move over a determined stroke so that in a first stage the pressure inside the pressure chamber is increased up to a transfer pressure immediately prior to the hollow needle passing through the septum, and in a second stage the hollow needle passes through the septum to open out into the distribution chamber that is at a pressure lower than the transfer pressure so that under the effect of this pressure difference a portion of the liquid is transferred from the container into said distribution chamber;
    wherein the distribution chamber includes a filter system for ensuring that a liquid phase is extracted from the liquid transferred into said chamber.

11. The device according to claim 10, wherein the approach system also enables the hollow needle and the septum to be separated relative to each other in such a manner that the hollow needle communicates with the inside of the pressure chamber so as to enable the fluid under pressure to cause any liquid contained in the hollow needle to be returned into the container.

12. The device according to claim 10, wherein the filter system includes a filter medium that lies at a distance from the septum so as to ensure that the liquid is distributed over the filter medium.

13. The device according to claim 12, wherein the filter medium is held in position on a support structure on which the filter medium rests.

14. The device according to claim 10, wherein the approach system comprises a cylinder for receiving a piston together defining the pressure chamber, the piston and the cylinder being movable in translation relative to each other.

15. The device according to claim 14, wherein the distribution chamber is defined by a portion of the cylinder for receiving the piston or by a separate unit containing a filter system and fitted to the cylinder.

16. The device according to claim 14, wherein the distal end of the hollow needle points away from the pressure chamber, and wherein the proximal end of the hollow needle extends inside the pressure chamber in a direction parallel to an approach and/or a separation direction.

17. The device according to claim 16, wherein the piston is provided with a protective sleeve surrounding the distal end of the hollow needle and defining a volume for receiving at least a portion of the container.

18. The device according to claim 17, wherein the septum is disposed at an end wall of the cylinder, in line with the proximal end of the hollow needle.

19. The device according to claim 10, further comprising a means for adjusting pressure in the pressure chamber as a function of the volume of fluid contained inside the container.

20. The device according to claim 10, comprising an abutment for limiting an approach movement in a predetermined position in which the proximal end of the hollow needle passes through the septum to open out into the distribution chamber.

* * * * *